(12) United States Patent
Wang et al.

(10) Patent No.: US 11,779,726 B2
(45) Date of Patent: Oct. 10, 2023

(54) ANESTHETIC EVAPORATOR LOCKING STRUCTURE AND ANESTHESIA MACHINE

(71) Applicants: SHENZHEN MINDRAY BIO-MEDICAL ELECTRONICS CO., LTD., Shenzhen (CN); Shenzhen Mindray Scientific Co., Ltd., Shenzhen (CN)

(72) Inventors: Congquan Wang, Shenzhen (CN); Peitao Chen, Shenzhen (CN); Sheng Wang, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 638 days.

(21) Appl. No.: 16/852,351

(22) Filed: Apr. 17, 2020

(65) Prior Publication Data

US 2020/0238043 A1 Jul. 30, 2020

Related U.S. Application Data

(63) Continuation of application No. PCT/CN2017/107132, filed on Oct. 20, 2017.

(51) Int. Cl.
*A61M 16/18* (2006.01)

(52) U.S. Cl.
CPC .................. *A61M 16/186* (2013.01)

(58) Field of Classification Search
CPC .......................................... A61M 16/18–186
See application file for complete search history.

(56) References Cited

U.S. PATENT DOCUMENTS

| 4,058,120 A | 11/1977 | Caparrelli et al. |
| 4,346,701 A | 8/1982 | Richards |

(Continued)

FOREIGN PATENT DOCUMENTS

| CN | 201735040 U | 2/2011 |
| CN | 102824678 A | 12/2012 |

(Continued)

OTHER PUBLICATIONS

European Search Report issued in related European Application No. 17929249.5, dated Oct. 9, 2020, 9 pages.

(Continued)

*Primary Examiner* — Rachel T Sippel
(74) *Attorney, Agent, or Firm* — BAYES PLLC

(57) ABSTRACT

An anesthetic evaporator locking structure for detachably connecting an anesthetic evaporator to an anesthesia main machine is disclosed. The anesthetic evaporator includes a main body and a securing member provided on the main body. The anesthesia main machine includes a driving element and a mating member provided on the anesthesia main machine. The securing member and the mating member mate with each other to form a primary locking mechanism, and when the anesthetic evaporator is in an activated state, the driving element limits the primary locking mechanism to realize secondary locking. The anesthetic evaporator further includes a handle provided on the main body and an unlocking device provided on the handle, and the unlocking device is used for unlocking the primary locking mechanism. The anesthetic evaporator locking structure can realize the double locking and has relatively high safety, and both the locking and unlocking processes can be operated by one hand, which is convenient and quick.

22 Claims, 9 Drawing Sheets

(56) References Cited

U.S. PATENT DOCUMENTS

| | | |
|---|---|---|
| 4,932,398 A | 6/1990 | Lancaster et al. |
| 4,982,734 A | 1/1991 | Green et al. |
| 5,520,168 A | 5/1996 | Whitaker |
| 6,302,104 B1 | 10/2001 | Kronekvist |
| 2006/0032502 A1 | 2/2006 | Gershteyn |

FOREIGN PATENT DOCUMENTS

| | | |
|---|---|---|
| CN | 103893889 A | 7/2014 |
| CN | 103899609 A | 7/2014 |
| EP | 0341917 A1 | 11/1989 |
| EP | 0898979 A1 | 3/1999 |
| GB | 2068238 A | 8/1981 |
| GB | 2276555 A | 10/1994 |
| WO | 8808317 A1 | 11/1988 |

OTHER PUBLICATIONS

First Office Action issued in related Chinese Application No. 201780096001.2, dated May 30, 2022, 8 pages.
International Search Report issued in corresponding International Application No. PCT/CN2017/107132, dated Jul. 12, 2018, 4 pages.

ANESTHETIC EVAPORATOR LOCKING STRUCTURE AND ANESTHESIA MACHINE

CROSS-REFERENCE TO RELATED APPLICATIONS

This application is a continuation of PCT Application NO. PCT/CN2017/107132, filed Oct. 20, 2017, entitled "ANESTHETIC EVAPORATOR LOCKING STRUCTURE AND ANESTHESIA MACHINE," the entire content of which is incorporated herein by reference.

TECHNICAL FIELD

This disclosure relates to the field of medical apparatuses, and in particular to an anesthetic evaporator locking structure and an anesthesia machine.

BACKGROUND

In order to facilitate production and subsequent maintenance, an anesthetic evaporator and an anesthesia main machine are usually detachable structures, and a locking device for fixing the anesthetic evaporator to the anesthesia main machine is designed. One solution is to provide a double mechanical lock on the anesthetic evaporator and the anesthesia main machine. After the anesthetic evaporator is installed in place on the anesthesia main machine, an unlocking handle is manually rotated to lock an unlocking button. When unlocking, the unlocking handle needs to be rotated before the unlocking button is pressed. However, this technical solution has a complicated unlocking step, and at the same time, the risk that the anesthetic evaporator is pulled out due to misoperation or forced unlocking during operation cannot be avoided, and the safety is low.

SUMMARY

Based on this, it is necessary to provide an anesthetic evaporator locking structure for the problems of tedious unlocking steps of an anesthetic evaporator, and low safety caused by the disengagement of the anesthetic evaporator from an anesthesia main machine because the anesthetic evaporator is pulled out during operation.

This disclosure provides an anesthetic evaporator locking structure for detachably connecting an anesthetic evaporator to an anesthesia main machine, wherein the anesthetic evaporator may include a main body, and the anesthesia main machine may include a driving element, the anesthetic evaporator locking structure may comprise a securing member provided on the main body and a mating member provided on the anesthesia main machine, wherein the securing member and the mating member may mate with each other to form a primary locking mechanism, and when the anesthetic evaporator is in an activated state, the driving element may limit the primary locking mechanism to realize a secondary locking; and the anesthetic evaporator further may include a handle provided on the main body and an unlocking device provided on the handle, and the unlocking device may be used for unlocking the primary locking mechanism.

The above anesthetic evaporator locking structure realizes the primary mechanical locking by the securing member provided on the anesthetic evaporator and the mating member provided on the anesthesia main machine mating with each other, and when the anesthetic evaporator is activated, the driving element provided on the anesthesia main machine may be synchronously started to compress the securing member, thereby realizing the secondary pneumatic control (electronic control) locking. Because the driving element and the anesthetic evaporator may be synchronously started or closed, the unlocking due to misoperation by an operator to disengage the anesthetic evaporator from the anesthesia main machine will not occur during the normal operation of the anesthetic evaporator, which can effectively improve the safety of an anesthesia machine using the anesthetic evaporator locking structure; and the above locking operation can be operated by one hand, which is convenient and quick. Furthermore, after the anesthetic evaporator stops operating, when the unlocking is needed, since the driving element has been closed while the anesthetic evaporator is closed, that is, the secondary locking is released, and by holding the handle with one hand and operating the unlocking device at the same time, the mating member can be disengaged from the securing member, thereby releasing the primary locking, and the unlocking process is convenient and quick.

In one embodiment, the driving element may compress the securing member to realize the secondary locking.

In one embodiment, the anesthetic evaporator further may include a compressing member provided on the main body, the compressing member may be movably connected with the main body, wherein the driving element may push the compressing member to move relative to the main body, such that the compressing member may be compressed against the securing member to realize the secondary locking.

In one embodiment, the compressing member may be rotatably connected with the main body; and the driving element may push the compressing member to rotate relative to the main body.

In one embodiment, the anesthetic evaporator further may include a reset element that may be connected with the compressing member and used for resetting the compressing member.

In one embodiment, the compressing member may be slidably connected with the main body; and the driving element may push the compressing member to move towards the securing member.

In one embodiment, the driving element may move relative to the main body and be compressed against the securing member to realize the secondary locking.

This disclosure is an anesthetic evaporator locking structure for detachably connecting an anesthetic evaporator with an anesthesia main machine, the anesthetic evaporator may include a main body, and the anesthesia main machine may include a driving element, the anesthetic evaporator locking structure may include a securing member provided on the main body and a mating member provided on the anesthesia main machine, wherein the securing member and the mating member may mate with each other to form a primary locking mechanism, and when the anesthetic evaporator is in an activated state, the driving element may be locked to the anesthetic evaporator.

In one embodiment, the unlocking device may include a pressing portion provided on the handle, the securing member may be connected with the handle, and include a free end and a locking end; the free end may be arranged opposite the pressing portion, and the locking end may mate with the mating member.

In one embodiment, the pressing portion may be pressed to drive the free end, such that the securing member may rotate relative to the handle to disengage the locking end from the mating member.

In one embodiment, the anesthetic evaporator further may include a first elastic member that may be provided between a side wall of the handle and the free end and used for resetting the securing member.

In one embodiment, the anesthetic evaporator further may include a second elastic member that may be provided between a side wall of the handle and the pressing portion and used for resetting the pressing portion.

In one embodiment, the anesthesia main machine may be provided with a guide rail, a sliding groove may be provided at a bottom of the anesthetic evaporator, and the guide rail may mate with the sliding groove.

In one embodiment, the mating member and the guide rail may be an integrated structure, and the securing member may be snap-fitted with the mating member when the anesthetic evaporator is advanced along the guide rail.

An anesthesia machine may include an anesthetic evaporator, an anesthesia main machine and an anesthetic evaporator locking structure described, the anesthetic evaporator locking structure may detachably connect the anesthetic evaporator to the anesthesia main machine.

BRIEF DESCRIPTION OF THE DRAWINGS

In order to more clearly illustrate technical solutions in the embodiments of this disclosure or in the prior art, a brief introduction to the drawings required for the description of the embodiments or the prior art will be provided below. Obviously, the drawings in the following description are only some of the embodiments of this disclosure, and those of ordinary skill in the art would also be able to obtain other drawings from these drawings without involving any inventive effort.

DETAILS DESCRIPTION

To make the objectives, technical solutions and advantages of this disclosure more clearly, this disclosure will be further described below in detail in conjunction with the accompanying drawings and the embodiments. It should be understood that the particular embodiments described herein are merely intended to explain this disclosure and do not limit the protection scope of this disclosure.

Figure 1:
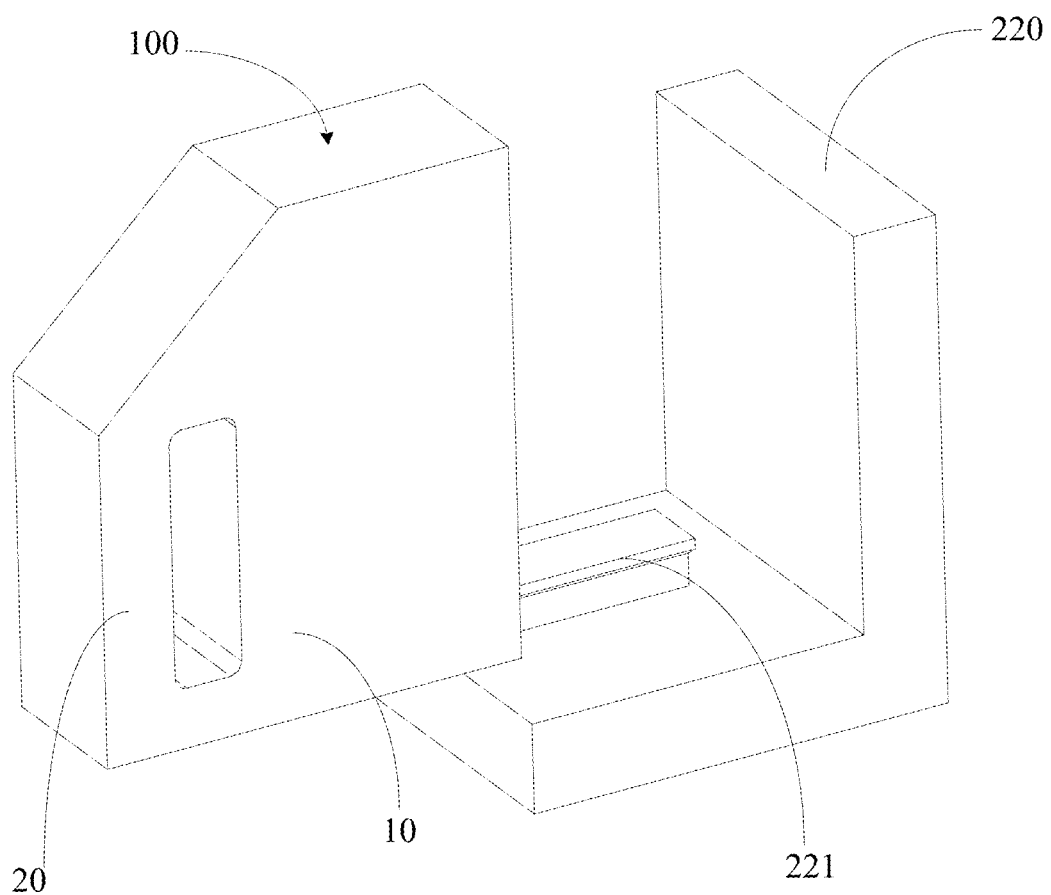
FIG. 1 is a schematic structural diagram of an anesthetic evaporator locking structure in one embodiment.

Referring to FIG. 1, an anesthetic evaporator locking structure may include an anesthetic evaporator 100 and an anesthesia main machine, and the anesthetic evaporator 100 may be detachably connected to the anesthesia main machine.

Relevant structures of the anesthetic evaporator 100 and corresponding structures of the anesthesia main machine may mate with each other to form a primary mechanical locking and secondary pneumatic control (electronic control) locking.

Figure 2:
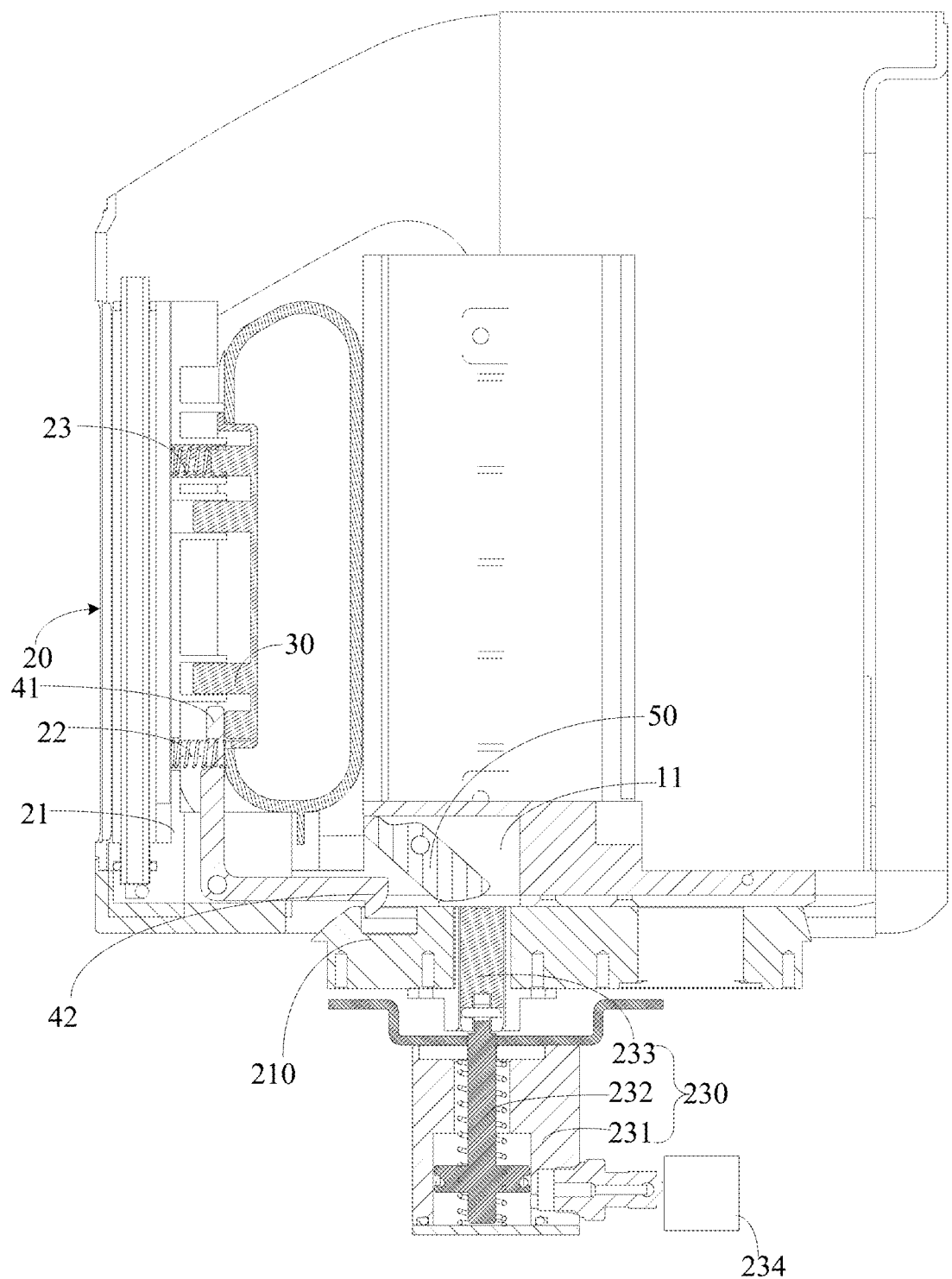
FIG. 2 is a schematic structural diagram of an anesthetic evaporator locking structure in one embodiment when realizing primary locking.

Referring to FIGS. 1 and 2, the anesthetic evaporator 100 may include a main body 10, a handle 20, a pressing portion 30 and a securing member 40, wherein the pressing portion 30 may serve as an unlocking device for unlocking a primary locking mechanism. The handle 20 may be provided on the main body 10, the pressing portion 30 may be provided on the handle 20, an accommodation cavity 21 may be formed inside the handle 20, the securing member 40 may be accommodated in the accommodation cavity 21, and the securing member 40 may be rotatably connected to an inner wall of the handle 20. After the anesthetic evaporator 100 is installed in place, the securing member 40 may mate with a relevant structure of the anesthesia main machine 10 to form primary locking, i.e. mechanical locking, and at this time, the anesthetic evaporator 100 pneumatically and electrically may communicate with the anesthesia main machine.

A second elastic member 23 may be provided between the pressing portion 30 and a side wall of the handle 20 to facilitate resetting the pressing portion 30.

The securing member 40 may include a free end 41 and a locking end 42 arranged at an included angle, the free end 41 may mate with the pressing portion 30, the joint of the free end 41 and the locking end 42 may be rotatably connected to the side wall of the handle 20, and the locking end 42 may mate with the relevant structure of the anesthesia main machine to form the primary locking. The pressing portion 30 may be pressed to touch the free end 41 to drive the securing member 40 to rotate, such that the locking end 42 may be disengaged from the relevant structure of the anesthesia main machine to realize unlocking. In order to facilitate resetting the securing member 40, a first elastic member 22 may be provided between the securing member 40 and the side wall of the handle 20. In one embodiment, the free end 41 and the locking end 42 may be of an integrated structure. As an alternative, the free end 41 and the locking end 42 can also be of independent structures having a connection relationship.

The anesthesia main machine may include a mounting seat 220 and a mating member 210 provided in the mounting seat 220. After the anesthetic evaporator 100 is installed in place on the mounting seat 220, the locking end 42 may be snap-fitted with the mating member 210, and the locking member 40 and the mating member 210 jointly form a first locking mechanism.

The mounting seat 220 may be provided with a guide rail 221, the bottom of the anesthetic evaporator 100 may be provided with a sliding groove, and when the anesthetic evaporator 100 is installed on the anesthesia main machine, the guide rail 221 and the sliding groove may mate with each other for positioning. The locking end 42 of the securing member 40 may extend into the sliding groove, the mating member 210 may be provided on the guide rail 221, and during the process of aligning the sliding groove of the anesthetic evaporator 100 with the guide rail 221 and advancing along the guide rail 221, the securing member 40 may be locked to the mating member 210. This process can be operated by one hand, which is convenient and quick. As an alternative to this embodiment, the mounting seat 220 may be provided with a sliding groove, a guide rail may be provided at the bottom of the anesthetic evaporator 100, and when the anesthetic evaporator 100 is installed on the anesthesia main machine, the guide rail and the sliding groove may mate with each other for positioning.

Figure 3:
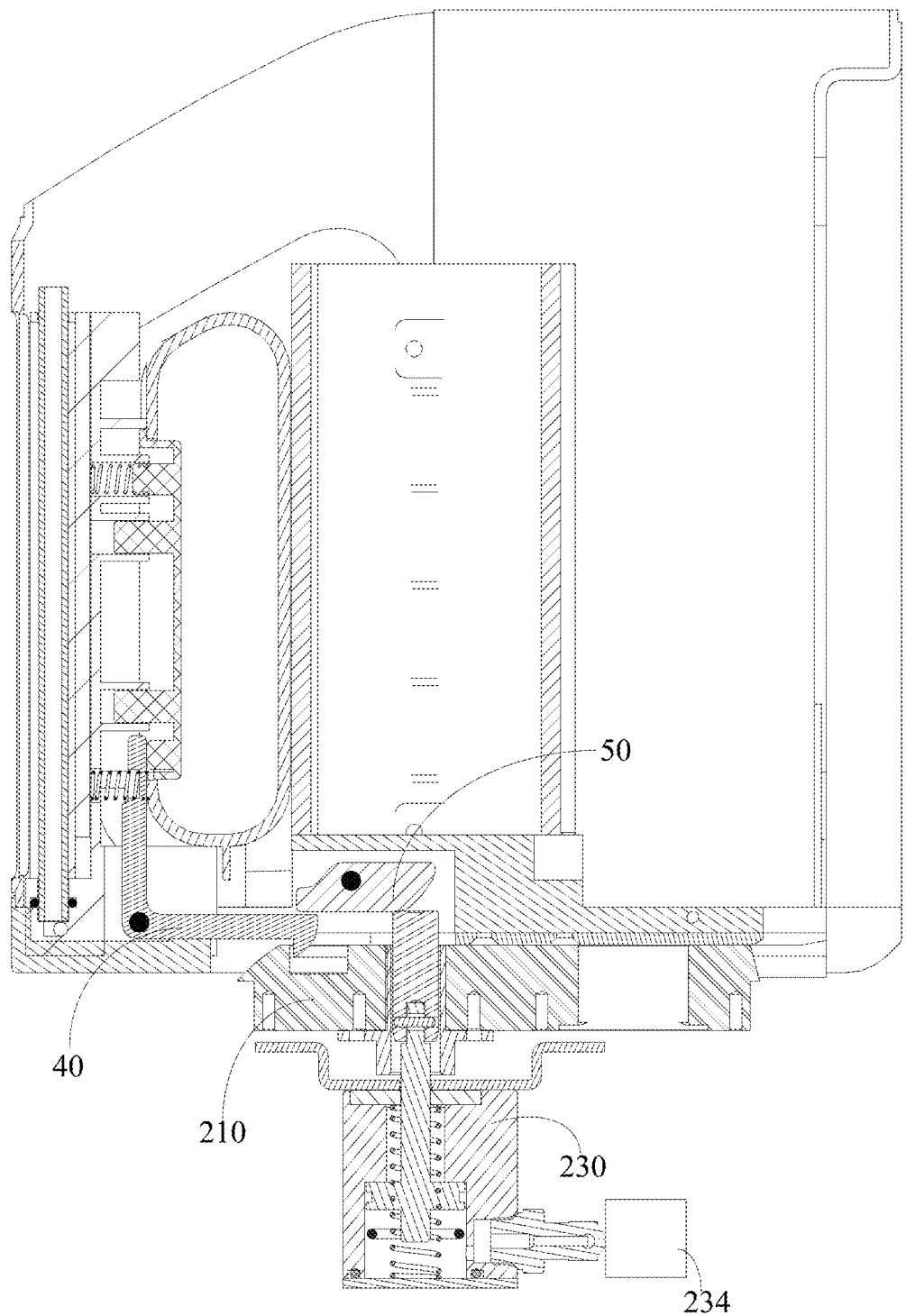
FIG. 3 is a schematic structural diagram of the anesthetic evaporator locking structure of FIG. 2 when realizing double locking.

In one embodiment, referring to FIGS. 2 and 3, the anesthetic evaporator 100 further may include a compressing member 50 provided at the bottom of the main body 10 and a reset element connected to the compressing member 50, the compressing member 50 may be rotatably connected to the main body 10, and the reset element may be fixedly connected to the main body 10. The anesthesia main machine may include a driving element 230, when the anesthetic evaporator 100 is placed on the anesthesia main machine, the locking end 42 may be snap-fitted with the mating member 210, at this time, the compressing member 50 may be adjacent to the driving element 230, and after the driving element 230 is started, the compressing member 50 may be driven to rotate, such that the compressing member 50 may be compressed against the locking end 42. The driving element 230 may mate with the compressing member 50 to realize secondary locking of the anesthetic evaporator 100 and the anesthesia main machine. When the anesthesia machine evaporator 100 is in a double locking state, since the securing member 40 may be compressed by the compressing member 50, an operator cannot press the pressing portion 30 to unlock, which effectively avoids misoperation, and can also remind the operator that the anesthetic evaporator 100 is in an operating state at this time. It can be understood that, as an alternative to this embodiment, the driving element 230 may drive the compressing member 50 to rotate, such that the compressing member 50 may be compressed against the mating member 210. The driving element 230 may mate with the compressing member 50 to realize secondary locking of the anesthetic evaporator 100 and the anesthesia main machine.

A control system in the anesthesia main machine may synchronously control the driving element 230 and the anesthetic evaporator 100. When the anesthetic evaporator 100 is activated, the driving element 230 may be synchronously started to realize secondary locking of the anesthetic evaporator 100. During the operation of the anesthetic evaporator 100, the disengagement of the anesthetic evaporator 100 from the anesthesia main machine due to misoperation by the operator will not occur. Furthermore, after the anesthetic evaporator 100 stops operating, when unlocking is needed, since the driving element 230 has been closed while the anesthetic evaporator 100 is closed, that is, the secondary locking is released, the pressing portion 30 is pressed, such that the securing member 40 is rotated relative to the main body 10 to disengage the locking end 42 from the mating member 210, thereby releasing the primary locking, and the unlocking can be operated by one hand, which is convenient and quick.

The bottom of the main body 10 may be provided with a mounting groove 11, the compressing member 50 may be accommodated in the mounting groove 11 and be rotatably connected to a side wall of the mounting groove 11. After being started, the driving element 230 may move towards the anesthetic evaporator 100, and when the compressing member 50 is pushed to rotate to a horizontal position, the compressing member 50 may be compressed against the locking end 42, realizing the secondary locking.

The driving element 230 can be a pneumatic control device, which may include a housing 231, a driving rod 232 partially accommodated in the housing 231, and a pushing rod 233 connected to the driving rod 232. The driving rod 232 may abut against an inner wall of the housing 231 and enclose a sealed space with the housing 231, and a high-pressure gas source 234 may be in communication with the sealed space. When the pneumatic control device is activated, the high-pressure gas source 234 may supply high-pressure gas into the sealed space, and the driving rod 232 and the pushing rod 233 may be pushed toward the anesthetic evaporator 100, the pushing rod 233 may abut against the compressing member 50 and push the compressing member 50 to rotate, thereby compressing same against the securing member 40.

When the anesthetic evaporator 100 needs to be removed, the anesthesia main machine may synchronously control the anesthetic evaporator 100 to stop operating while sending a shutdown signal to the driving element 230, at this time, the high-pressure gas may be discharged from the sealed space, the driving rod 232 and the pushing rod 233 may return to their original positions, and under the action of the reset element, the compressing member 50 may rotate in a reverse direction, and the locking end 42 may be released; and the pressing portion 30 may be pressed to drive the securing member 40 to rotate, such that the locking end 42 may be disengaged from the mating member 210, and the anesthetic evaporator 100 can be removed from the anesthesia main machine.

The driving element 230 can also be an electric control device, which may include an iron core and a coil wound around the iron core. The iron core may be connected to the pushing rod 233, when the coil is energized, a magnetic force may be generated, the iron core and the pushing rod 233 may be pushed to move upward to rotate the compressing member 50 to a horizontal position, and when the main machine sends a shutdown signal, the coil may lose power and the iron core and the pushing rod 233 may automatically reset, and the compressing member 50 may be rotated to an initial position and disengaged from the securing member 40.

When the anesthetic evaporator 100 needs to be removed, the anesthesia main machine synchronously may control the anesthetic evaporator 100 to stop operating while sending a shutdown signal to the driving element 230, at this time, a magnetic attraction force of the iron core to the compressing member 40 may disappear, and under the action of the reset element, the compressing member 50 may rotate in the reverse direction, and the locking end 42 may be released; and the pressing portion 30 may be pressed to drive the securing member 40 to rotate, such that the locking end 42 may be disengaged from the mating member 210, and the anesthetic evaporator 100 can be removed from the anesthesia main machine.

Figure 4:
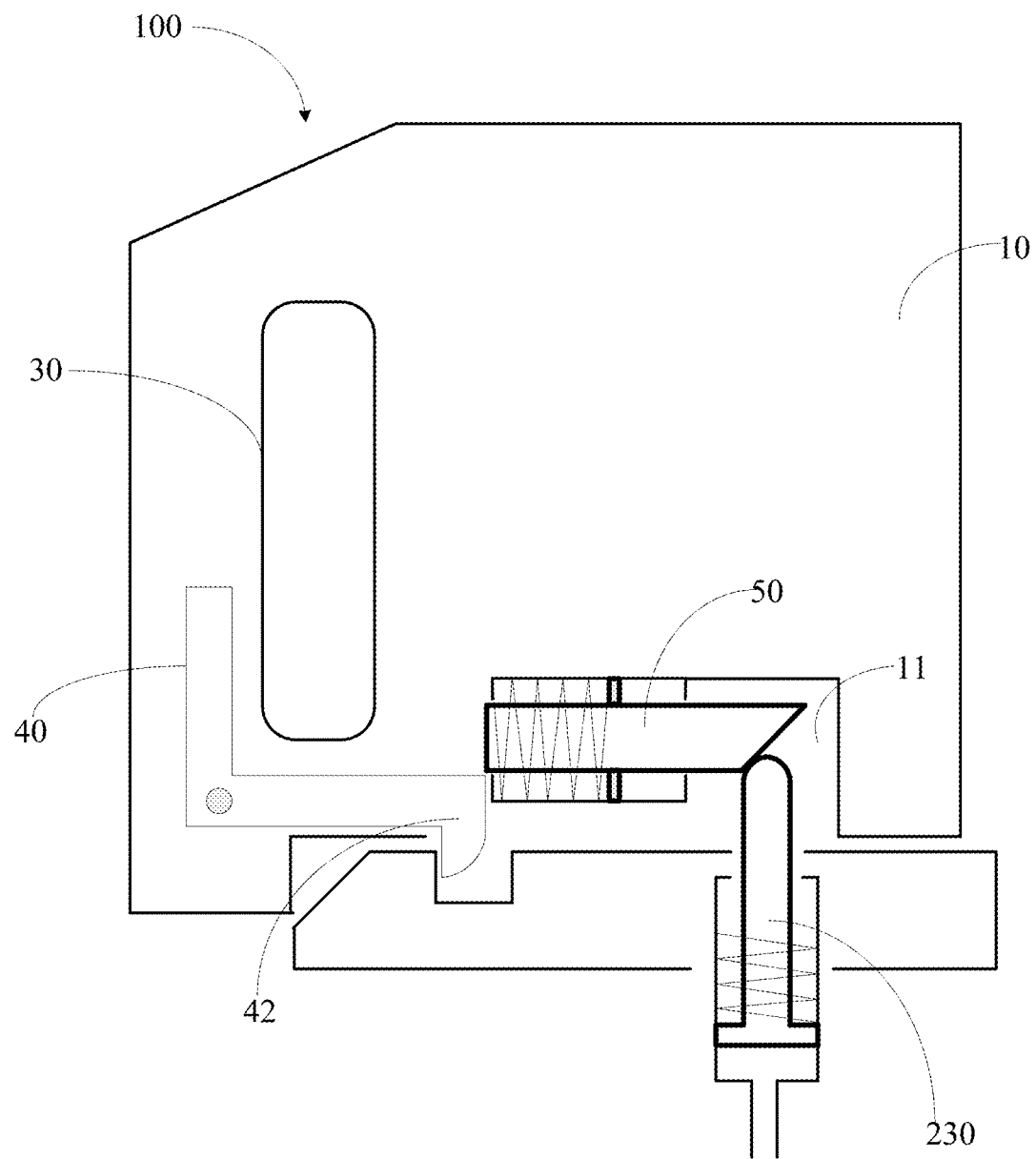
FIG. 4 is a schematic structural diagram of an anesthetic evaporator locking structure in another embodiment when realizing primary locking.
Figure 5:
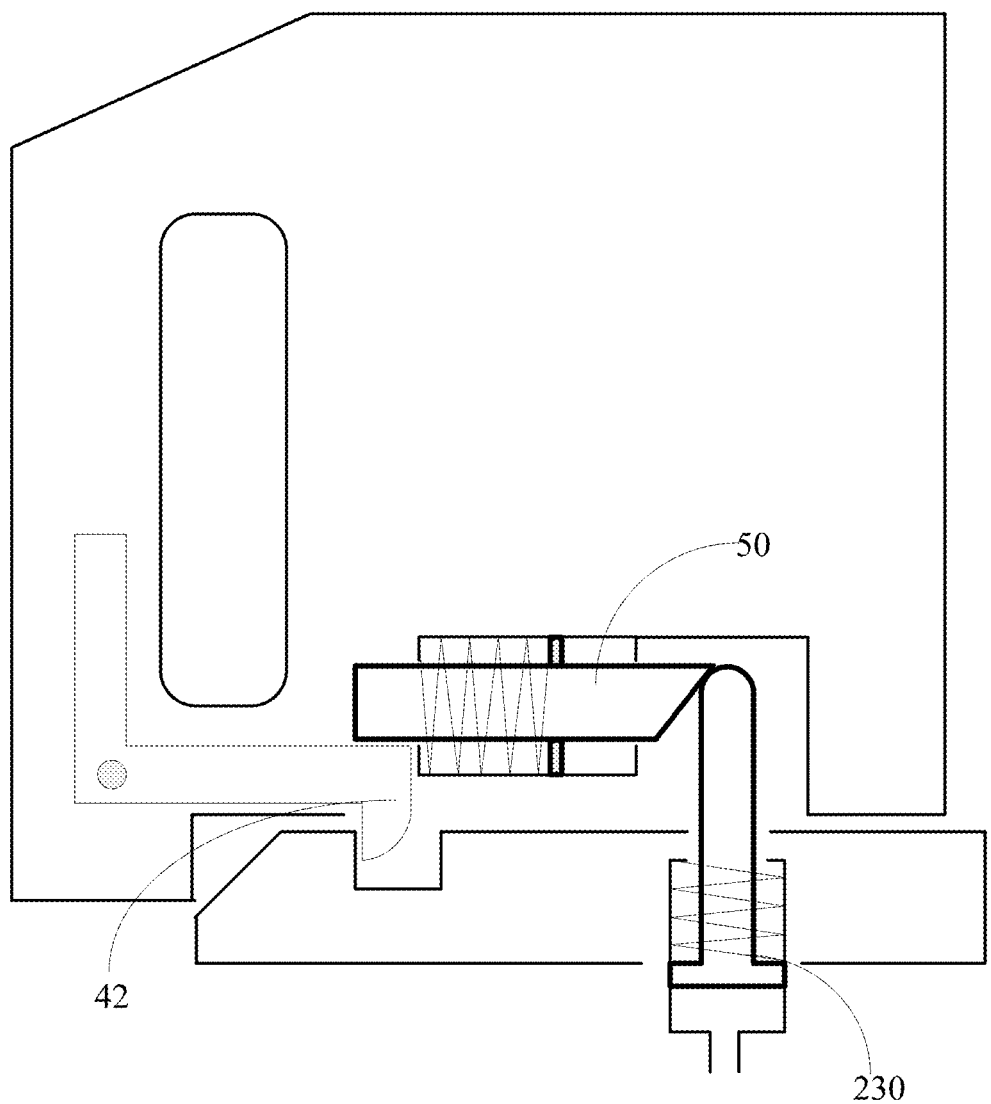
FIG. 5 is a schematic structural diagram of the anesthetic evaporator locking structure of FIG. 4 when realizing double locking.

In one embodiment, referring to FIGS. 4 and 5, as a substitute of the rotational connection of the compressing member 50 and the main body 10, the compressing member 50 may be slidably connected to the main body 10, and the anesthesia main machine may include a driving element 230.

A mounting groove 11 may be formed at the bottom of the main body 10, and the compressing member 50 may be accommodated in the mounting groove 11 and may be slidably connected to a bottom wall of the mounting groove 11. After being started, the driving element 230 may move in a perpendicular direction, and the compressing member 50 may be pushed to move in a direction close to the securing member 40 until the compressing member 50 may be compressed against the locking end 42, realizing the secondary locking. As an alternative to this embodiment, the driving element 230 may push the compressing member 50 to be compressed against the mating member, realizing the secondary locking.

The driving element 230 can be a pneumatic control device, which may include a cavity, a driving rod partially accommodated in the cavity, and a pushing rod connected to the driving rod. The driving rod may abut against an inner wall of the cavity and enclose a sealed space with the cavity, and a high-pressure gas source may be in communication with the sealed space. When the pneumatic control device is activated, the high-pressure gas source may supply high-pressure gas into the sealed space, and the driving rod and the pushing rod may be pushed to move in a horizontal direction, the pushing rod may abut against the compressing member 50 and pushes the compressing member 50 to move in the direction close to the securing member 40, thereby compressing same against the securing member 40.

When the anesthetic evaporator 100 needs to be removed, the anesthesia main machine synchronously may control the anesthetic evaporator 100 to stop operating while sending a shutdown signal to the driving element 230, at this time, the driving rod and the pushing rod may return to their original positions, and under the action of the reset element, the compressing member 50 may move in a direction away from the securing member 40, and the locking end 42 may be released; and the pressing portion 30 may be pressed to drive the securing member 40 to rotate, such that the locking end 42 may be disengaged from the mating member 210, and the anesthetic evaporator 100 can be removed from the anesthesia main machine.

Other structures are the same as those in the first embodiment, and will not be described again.

Figure 6:
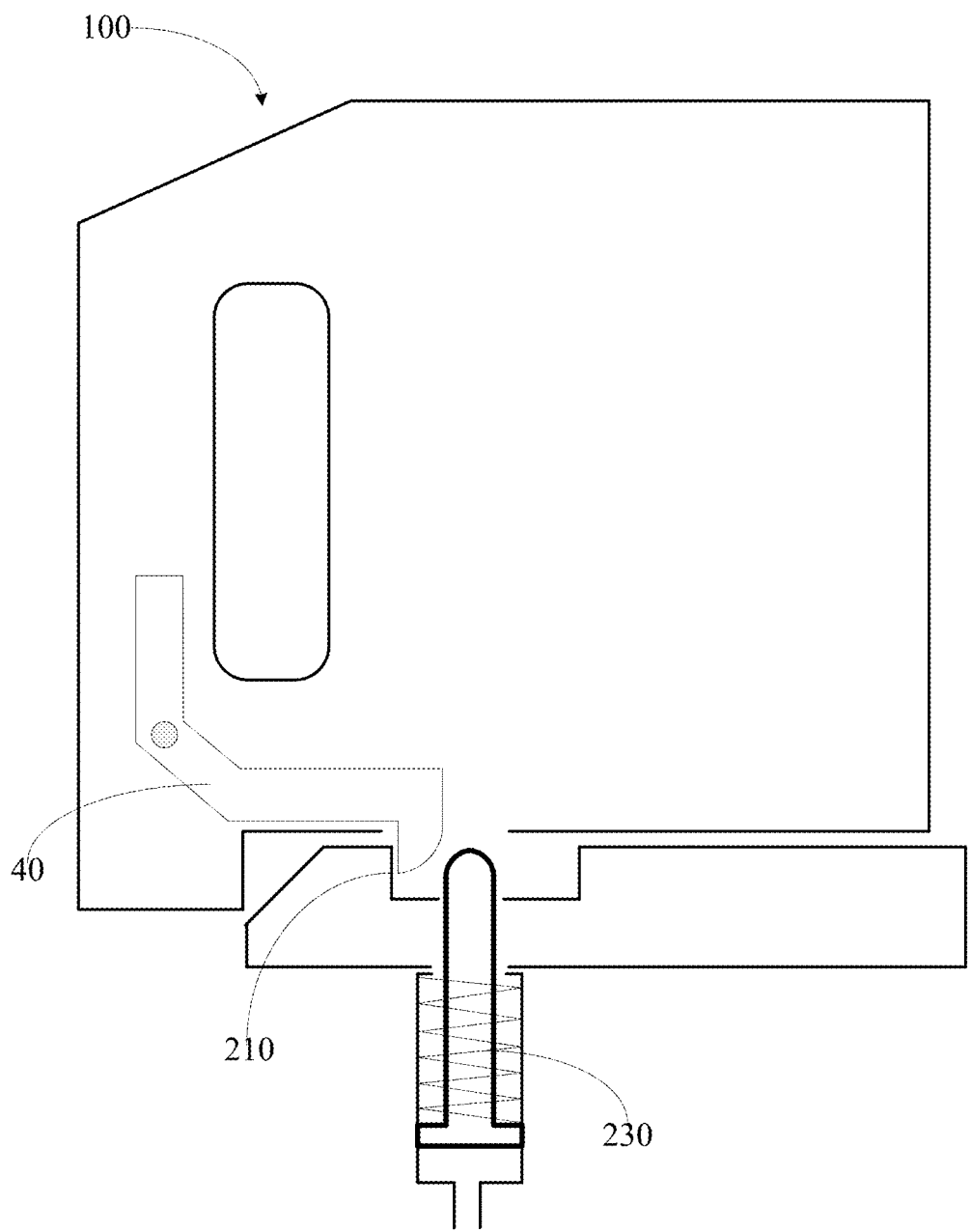
FIG. 6 is a schematic structural diagram of an anesthetic evaporator locking structure in still another embodiment when realizing primary locking.
Figure 7:
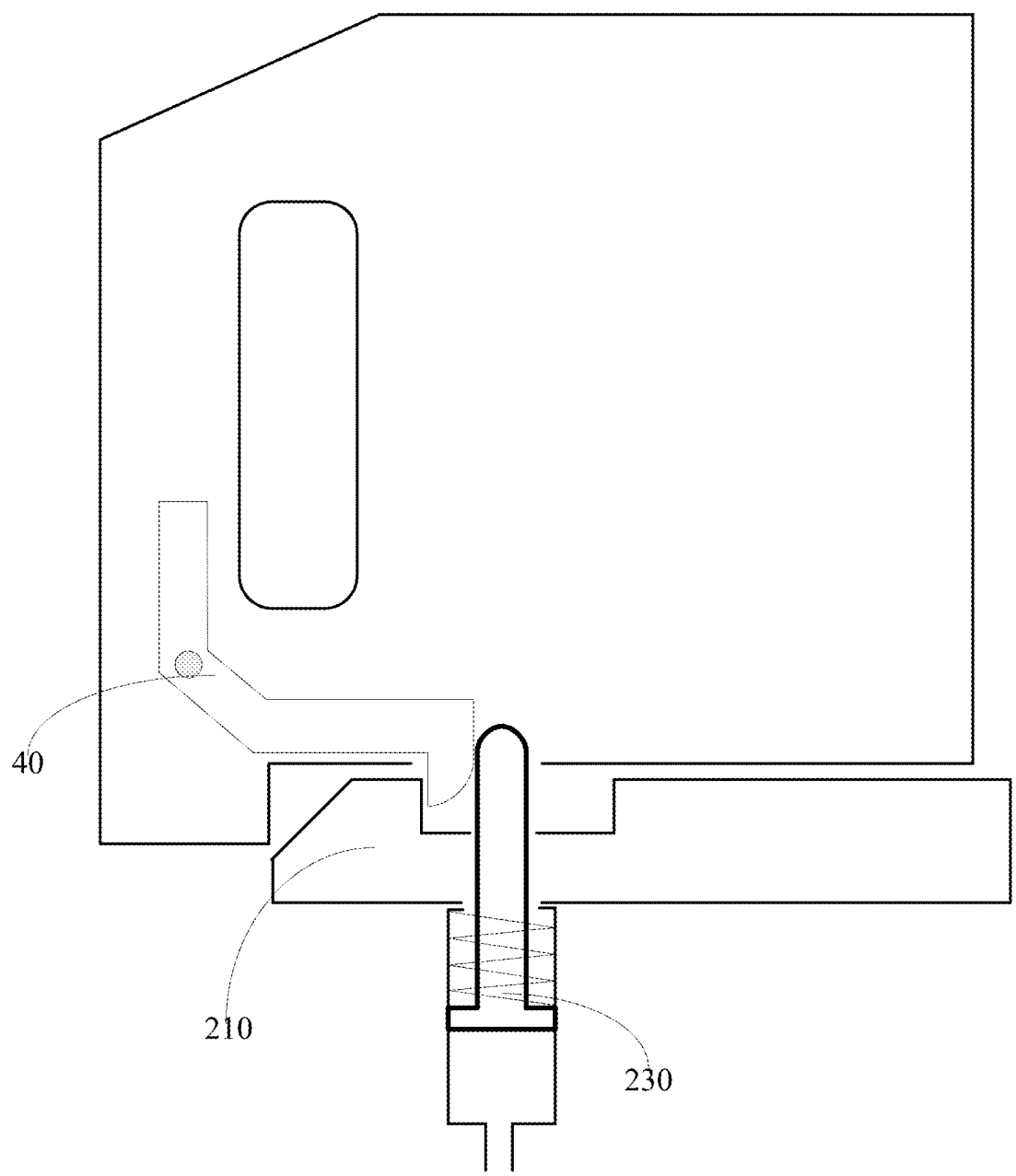
FIG. 7 is a schematic structural diagram of the anesthetic evaporator locking structure of FIG. 6 when realizing double locking.

In one embodiment, referring to FIGS. 6 and 7, the function of the compressing member 50 can also be replaced by other elements. For example, the anesthetic evaporator 100 may include a securing member 40, the anesthesia main machine may include a mating member 210 and a driving element 230, and the mating member 210 and the securing member 40 may mate with each other to realize the primary locking. After being started, the driving element 230 may move in a direction close to the securing member 40. In particular, an end of the driving element 230 may be compressed against the securing member 40 to realize the secondary locking. In this embodiment, the driving element 230 may move in a vertical direction, and other structures may be the same as those in the first embodiment, and will not be described again.

Figure 8:
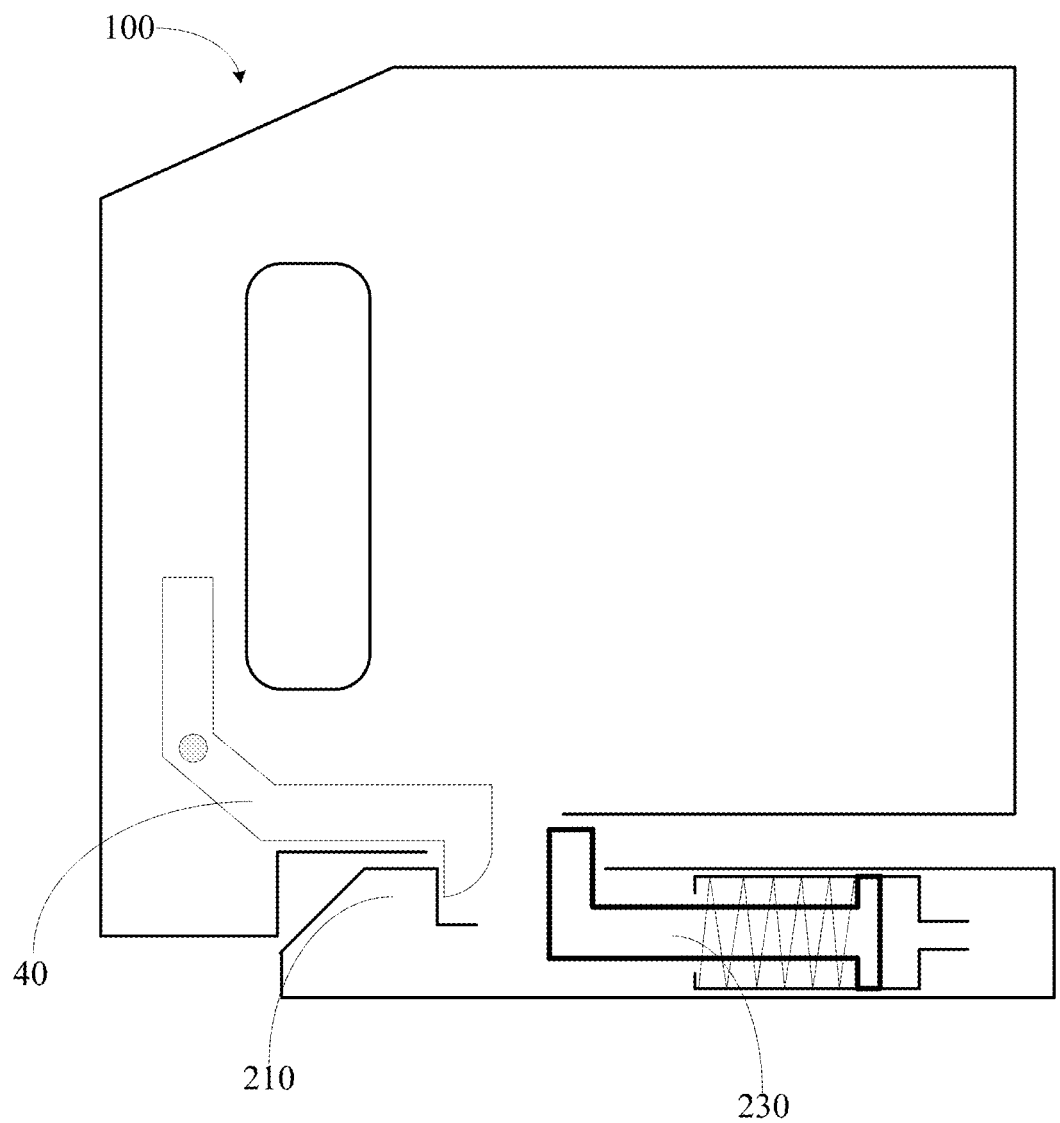
FIG. 8 is a schematic structural diagram of an anesthetic evaporator locking structure in yet another embodiment when realizing primary locking.
Figure 9:
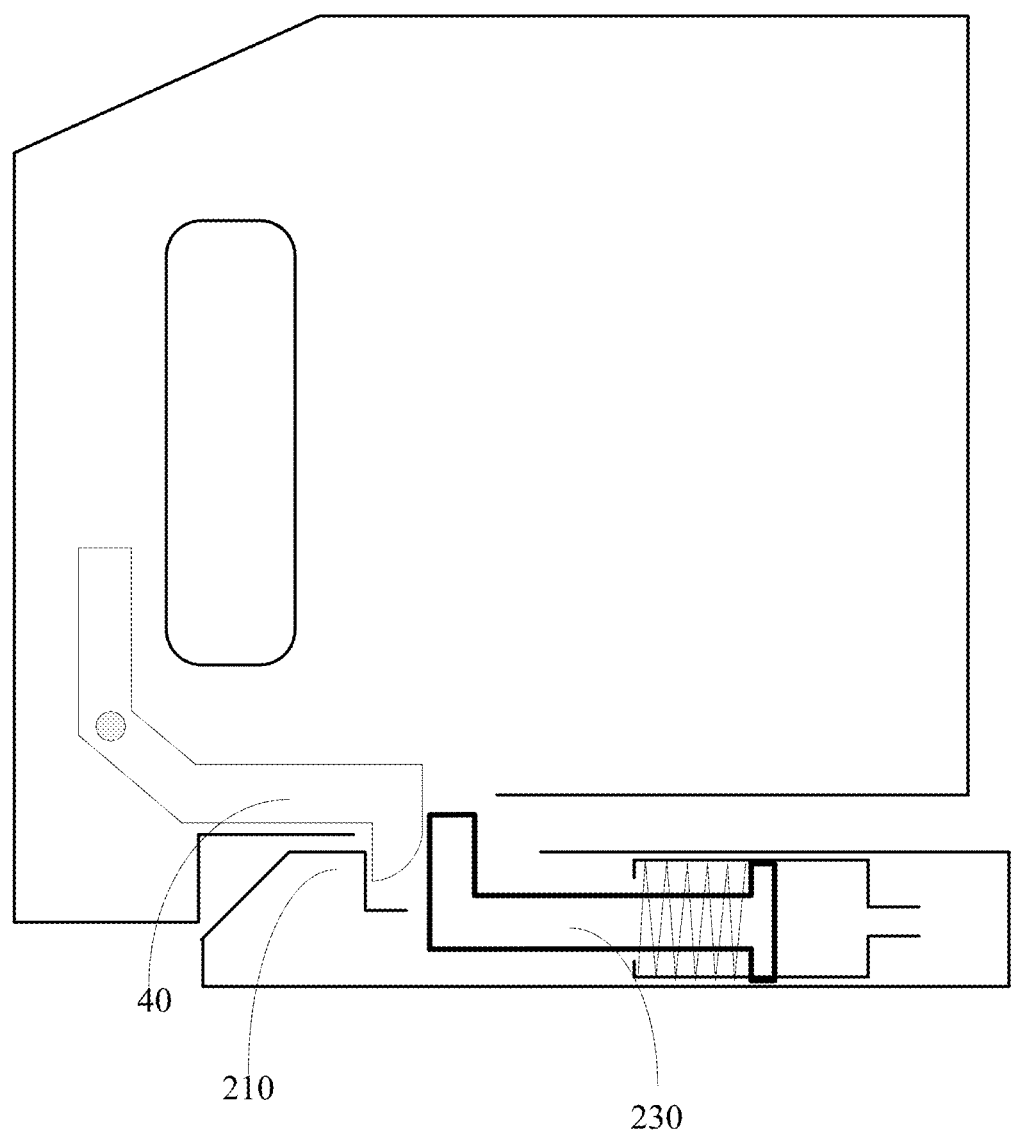
FIG. 9 is a schematic structural diagram of the anesthetic evaporator locking structure of FIG. 8 when realizing double locking.

In one embodiment, referring to FIGS. 8 and 9, the function of the compressing member 50 may be replaced by a driving element 230, and the driving element 230 may move in a horizontal direction. The anesthetic evaporator 100 may include a securing member 40, the anesthesia main machine may include a mating member 210 and a driving element 230, and the mating member 210 and the securing member 40 may mate with each other to realize the primary locking. After being started, the driving element 230 may move in a direction close to the securing member 40. In particular, an end of the driving element 230 may be compressed against the securing member 40 to realize the secondary locking. Other structures are the same as those in the first embodiment, and will not be described again.

In one embodiment, after the anesthetic evaporator 100 is installed in place on the mounting seat 220, the locking end 42 may be snap-fitted with the mating member 210, and the locking member 40 and the mating member 210 may jointly form a first locking mechanism, realizing the primary locking. The anesthetic evaporator 100 is activated, the driving element 230 may be synchronously started, move upward, and be locked to the anesthetic evaporator 100, realizing double locking. When the anesthetic evaporator 100 is in an activated state, the driving element 230 will not be unlocked, thereby avoiding the disengagement of the anesthetic evaporator 100 from the anesthesia main machine due to misoperation by the operator.

The various technical features of the embodiments described above can be arbitrarily combined. In order to simplify the description, all possible combinations of the various technical features in the above embodiments have not been described. However, any combination of these technical features should be considered to fall within the scope of the disclosure of this description as long as there is no contradiction.

Only several implementations of this disclosure are described in the foregoing embodiments. The descriptions are relatively detailed and specific, but cannot be construed as a limitation on the patent scope of this disclosure. It should be noted that a person of ordinary skill in the art could also make several variations and improvements without departing from the concept of this disclosure. These variations and improvements all fall within the scope of protection of this disclosure. Therefore, the scope of protection of this patent of disclosure shall be in accordance with the appended claims.

What is claimed is:

1. An anesthetic evaporator locking structure, configured for detachably connecting an anesthetic evaporator having a main body to an anesthesia main machine having a driving element, wherein
   the anesthetic evaporator locking structure comprises:
   a securing member provided on the main body and a mating member provided on the anesthesia main machine, wherein the securing member and the mating member mate with each other to form a primary locking mechanism, and activation of the anesthetic evaporator, synchronously activates the driving element of the anesthesia main machine to form a secondary locking to limit the primary locking mechanism; and
   the anesthetic evaporator further comprises a handle provided on the main body and an unlocking device provided on the handle, and the unlocking device is used for unlocking the primary locking mechanism.

2. The anesthetic evaporator locking structure of claim 1, wherein the driving element compresses the securing member to realize the secondary locking.

3. The anesthetic evaporator locking structure of claim 2, wherein the anesthetic evaporator further comprises a compressing member provided on the main body, the compressing member being movably connected with the main body, wherein the driving element pushes the compressing member to move relative to the main body, such that the compressing member is compressed against the securing member to realize the secondary locking.

4. The anesthetic evaporator locking structure of claim 3, wherein the compressing member is rotatably connected with the main body; and wherein the driving element pushes the compressing member to rotate relative to the main body.

5. The anesthetic evaporator locking structure of claim 4, wherein the anesthetic evaporator further comprises a reset element that is connected with the compressing member and used for resetting the compressing member.

6. The anesthetic evaporator locking structure of claim 1, wherein the unlocking device comprises a pressing portion provided on the handle, the securing member is connected with the handle, and the securing member comprises a free end and a locking end, wherein the free end is arranged opposite the pressing portion, and the locking end mates with the mating member.

7. The anesthetic evaporator locking structure of claim 6, wherein the pressing portion is pressed to drive the free end, such that the securing member rotates relative to the handle to disengage the locking end from the mating member.

8. The anesthetic evaporator locking structure of claim 6, wherein the anesthetic evaporator further comprises a first elastic member, which is provided between a side wall of the handle and the free end and used for resetting the securing member.

9. The anesthetic evaporator locking structure of claim 6, wherein the anesthetic evaporator further comprises a second elastic member, which is provided between a side wall of the handle and the pressing portion and used for resetting the pressing portion.

10. The anesthetic evaporator locking structure of claim 1, wherein the anesthesia main machine is provided with a guide rail, a sliding groove is provided at a bottom of the anesthetic evaporator, and the guide rail mates with the sliding groove.

11. The anesthetic evaporator locking structure of claim 10, wherein the mating member and the guide rail form an integrated structure, and the securing member is snap-fitted with the mating member when the anesthetic evaporator is advanced along the guide rail.

12. An anesthesia machine, comprising the anesthetic evaporator, the anesthesia main machine and the anesthetic evaporator locking structure of claim 1, the anesthetic evaporator locking structure detachably connecting the anesthetic evaporator to the anesthesia main machine.

13. The anesthetic evaporator locking structure of claim 3, wherein the compressing member is slidably connected with the main body; and wherein the driving element pushes the compressing member to move towards the securing member.

14. The anesthetic evaporator locking structure of claim 2, wherein the driving element moves relative to the main body and is compressed against the securing member to realize the secondary locking.

15. An anesthetic evaporator locking structure, configured for detachably connecting an anesthetic evaporator having a main body to an anesthesia main machine having a driving element, wherein
the anesthetic evaporator locking structure comprises:
a securing member provided on the main body, the securing member having a free end and a locking end; and
a mating member provided on the anesthesia main machine, wherein the locking end of the securing member and the mating member mate with each other to form a primary locking mechanism, and activation of the anesthetic evaporator synchronously activates the driving element of the anesthesia main machine to lock with the anesthetic evaporator.

16. The anesthetic evaporator locking structure of claim 15, wherein:
the anesthetic evaporator further comprises a handle provided on the main body and an unlocking device provided on the handle, and the unlocking device is used for unlocking the primary locking mechanism;
the unlocking device comprises a pressing portion provided on the handle;
the securing member is connected with the handle; and
the free end is arranged opposite the pressing portion, and the locking end mates with the mating member.

17. The anesthetic evaporator locking structure of claim 16, wherein the pressing portion is pressed to drive the free end, such that the securing member rotates relative to the handle to disengage the locking end from the mating member.

18. The anesthetic evaporator locking structure of claim 16, wherein the anesthetic evaporator further comprises a first elastic member that is provided between a side wall of the handle and the free end, and the first elastic member is used for resetting the securing member.

19. The anesthetic evaporator locking structure of claim 16, wherein the anesthetic evaporator further comprises a second elastic member that is provided between a side wall of the handle and the pressing portion, and the second elastic member is used for resetting the pressing portion.

20. The anesthetic evaporator locking structure of claim 15, wherein the anesthesia main machine is provided with a guide rail, a sliding groove is provided at a bottom of the anesthetic evaporator, and the guide rail mates with the sliding groove.

21. The anesthetic evaporator locking structure of claim 20, wherein the mating member and the guide rail form an integrated structure, and the securing member is snap-fitted with the mating member when the anesthetic evaporator is advanced along the guide rail.

22. An anesthesia machine, comprising the anesthetic evaporator, the anesthesia main machine and the anesthetic evaporator locking structure of claim 15, the anesthetic evaporator locking structure detachably connecting the anesthetic evaporator to the anesthesia main machine.

* * * * *